US011627997B1

(12) United States Patent
Zook

(10) Patent No.: US 11,627,997 B1
(45) Date of Patent: Apr. 18, 2023

(54) LUMBAR SPINOUS PROCESS STATIC AND DYNAMIC STABILIZATION DEVICE

(71) Applicant: Jason Zook, Valdese, NC (US)

(72) Inventor: Jason Zook, Valdese, NC (US)

( * ) Notice: Subject to any disclaimer, the term of this patent is extended or adjusted under 35 U.S.C. 154(b) by 0 days.

(21) Appl. No.: 17/485,923

(22) Filed: Sep. 27, 2021

Related U.S. Application Data

(60) Provisional application No. 63/086,287, filed on Oct. 1, 2020.

(51) Int. Cl.
*A61B 17/70* (2006.01)

(52) U.S. Cl.
CPC ...... *A61B 17/7067* (2013.01); *A61B 17/7068* (2013.01)

(58) Field of Classification Search
CPC ............ A61B 17/7067; A61B 17/7068; A61B 17/7065; A61B 17/707; A61B 17/7064; A61B 17/7062; A61B 17/8004
See application file for complete search history.

(56) References Cited

U.S. PATENT DOCUMENTS 6,126,660 A * 10/2000 Dietz .................. A61B 17/025 606/90
2002/0116000 A1* 8/2002 Zucherman ........ A61B 17/7062 606/279
2003/0167059 A1* 9/2003 Young ................ A61B 17/7014 606/258
2004/0102778 A1* 5/2004 Huebner ........... A61B 17/1728 606/71
2006/0142767 A1* 6/2006 Green .................... A61B 17/80 606/281
2006/0241601 A1* 10/2006 Trautwein .......... A61B 17/7049 606/279
2007/0100340 A1* 5/2007 Lange ................ A61B 17/7065 606/279
2007/0270827 A1* 11/2007 Lim .................. A61B 17/7062 606/86 A
2008/0234733 A1* 9/2008 Scrantz .............. A61B 17/7062 606/151
2010/0106190 A1* 4/2010 Linares .............. A61B 17/7067 606/249

(Continued)

FOREIGN PATENT DOCUMENTS

WO WO-2015072655 A1 * 5/2015 ......... A61B 17/7065

*Primary Examiner* — Jan Christopher L Merene
*Assistant Examiner* — Anna V. Little
(74) *Attorney, Agent, or Firm* — Stites & Harbison, PLLC; David W. Nagle, Jr.; Gary N. Stewart

(57) ABSTRACT

A lumbar process static and dynamic stabilization device includes: an upper arm configured to receive and be affixed to a first spinous process of one vertebrae; and a lower arm configured to receive and be affixed to a second spinous process of another vertebrae. The upper arm and the lower arm are pivotally connected, such that the upper arm and the lower arm can pivot relative to each other to transition the device to a desired orientation. At the same time, the device can be selectively locked into either a static configuration by a locking mechanism or allowed to move dynamically, such that the upper arm and the lower arm of the device are allowed to move relative to each other in response to manipulation of the portion of the lumbar spine on which the device is implemented.

13 Claims, 17 Drawing Sheets

(56) References Cited

U.S. PATENT DOCUMENTS

| | | | | |
|---|---|---|---|---|
| 2011/0087286 | A1* | 4/2011 | Ciupik | A61B 17/7065 606/279 |
| 2011/0118788 | A1* | 5/2011 | Hochschuler | A61B 17/7065 606/279 |
| 2011/0172709 | A1* | 7/2011 | Lyons | A61B 17/7068 606/248 |
| 2015/0012040 | A1* | 1/2015 | Agarwal | A61B 17/7068 606/248 |
| 2016/0022324 | A1* | 1/2016 | Yoon | A61B 17/7062 606/252 |
| 2018/0078288 | A1* | 3/2018 | Omar-Pasha | A61B 17/707 |

* cited by examiner

LUMBAR SPINOUS PROCESS STATIC AND DYNAMIC STABILIZATION DEVICE

CROSS-REFERENCE TO RELATED APPLICATIONS

The present application claims priority to U.S. Patent Application Ser. No. 63/086,287 filed on Oct. 1, 2020, the entire disclosure of which is incorporated herein by reference.

BACKGROUND OF THE INVENTION

Spinal fusion is a surgical procedure in which two or more vertebrae are joined (or fused) into a single structure. In general, spinal fusion is used to decompress and stabilize the spine by preventing any movement of the fused vertebrae relative to one another. Spinal fusion commonly requires the use of certain hardware (e.g., plates, screws, etc.), in combination with bone grafts or artificial bone substitutes, to fuse the vertebrae.

A laminectomy is a surgical procedure in which a portion of the lamina (which is a posterior arch of the vertebral bone) is removed. A laminectomy can be used to treat spinal stenosis by relieving pressure on the spinal cord. A laminectomy is also commonly performed to permit the removal or reshaping of a spinal disc as part of a treatment for a herniated, bulging, or degenerated spinal disc.

Although a wide range of devices exist in the art, such devices are designed only for stabilization for fusion or to stabilize a partial laminectomy. There are no known devices that can be used both in a stabilized, fusion supplementation and in a dynamic (non-fusion) setting as a stabilizing device for a lumbar laminectomy.

SUMMARY OF THE INVENTION

The present invention is a lumbar process static and dynamic stabilization device for use both in a stabilized, fusion supplementation and in a dynamic (non-fusion) setting as a stabilizing device for a lumbar laminectomy.

An exemplary lumbar process static and dynamic stabilization device made in accordance with the present invention is, in use, affixed to two spinous processes of a lumbar spine, spanning across one or more vertebrae interspaces. Thus, in some embodiments, the length of the device is adjustable to provide a construct that can extend between the spinous processes of two directly adjacent vertebrae or can extend across multiple vertebrae interspaces.

An exemplary lumbar process static and dynamic stabilization device made in accordance with the present invention generally includes: an upper arm configured to receive and be affixed to a first spinous process of one vertebrae; and a lower arm configured to receive and be affixed to a second spinous process of another vertebrae. The upper arm and the lower arm are pivotally connected, such that the upper arm and the lower arm can pivot relative to each other to transition the device to a desired orientation. At the same time, the device can be selectively locked into either a static configuration by a locking mechanism or allowed to move dynamically, such that the upper arm and the lower arm of the device are allowed to move relative to each other in response to manipulation of the portion of the lumbar spine on which the device is implemented. The device of the present invention can thus function as either a fixed-angle or variable angle construct, such that it can be utilized in fusion-based applications or settings (e.g., to supplement anterior instrumentation during lumbar fusion) and non-fusion-based applications or settings alike.

In some embodiments, the upper arm can be characterized as including: a base, which is secured to the lower arm; and a brace, which is configured to receive and be affixed to a first target spinous process. In this regard, the brace of the upper arm has a shape similar to that of a stirrup, with a first side portion and a second side portion which define a cavity in which the first spinous process is received. The first side portion and second side portion may be provided with openings, so that bicortical or unicortical screws can be inserted as necessary through the first side portion and/or the second side portion to secure the first spinous process in the cavity of the brace of the upper arm. Furthermore, the interior surfaces of the first and second side portions of the brace may also be provided with bone spikes to further assist in securing the brace of the upper arm to the first spinous process.

Similarly, in some embodiments, the lower arm can be characterized as including: a base, which is secured to the upper arm; and a brace, which is configured to receive and be affixed to a second target spinous process. In this regard, the brace of the lower arm also has a shape similar to that of a stirrup, with a first side portion and a second side portion which define a cavity in which the second spinous process is received. The first side portion and second side portion may be provided with openings, so that bicortical or unicortical screws can be inserted as necessary through the first side portion and/or the second side portion to secure the second spinous process in the cavity of the brace of the lower arm. Furthermore, the interior surfaces of the first and second side portions of the brace may also be provided with bone spikes to further assist in securing the brace of the lower arm to the second spinous process.

With respect to each of the upper arm and the lower arm, in some embodiments, a distance between the first side portion and the second side portion can be adjusted, widening or narrowing the cavity configured to receive the first spinous process or the second spinous process of the spine.

Furthermore, as noted above, in some embodiments, the length of the device is adjustable to provide a construct that can extend between the spinous processes of two directly adjacent vertebrae or can extend across multiple vertebrae interspaces. Such adjustment may be achieved via adjustment of the positioning of the brace relative to the base of either or both of the upper arm and the lower arm. For instance, in some embodiments, movement of the brace relative to the base is accomplished by a rack-and-pinion arrangement. Once the device has been set to a desired length, the positioning of the pinion along the rack can be fixed via a locking mechanism.

DETAILED DESCRIPTION OF THE INVENTION

The present invention is a lumbar process static and dynamic stabilization device for use both in a stabilized, fusion supplementation and in a dynamic (non-fusion) setting as a stabilizing device for a lumbar laminectomy.

Figure 1:
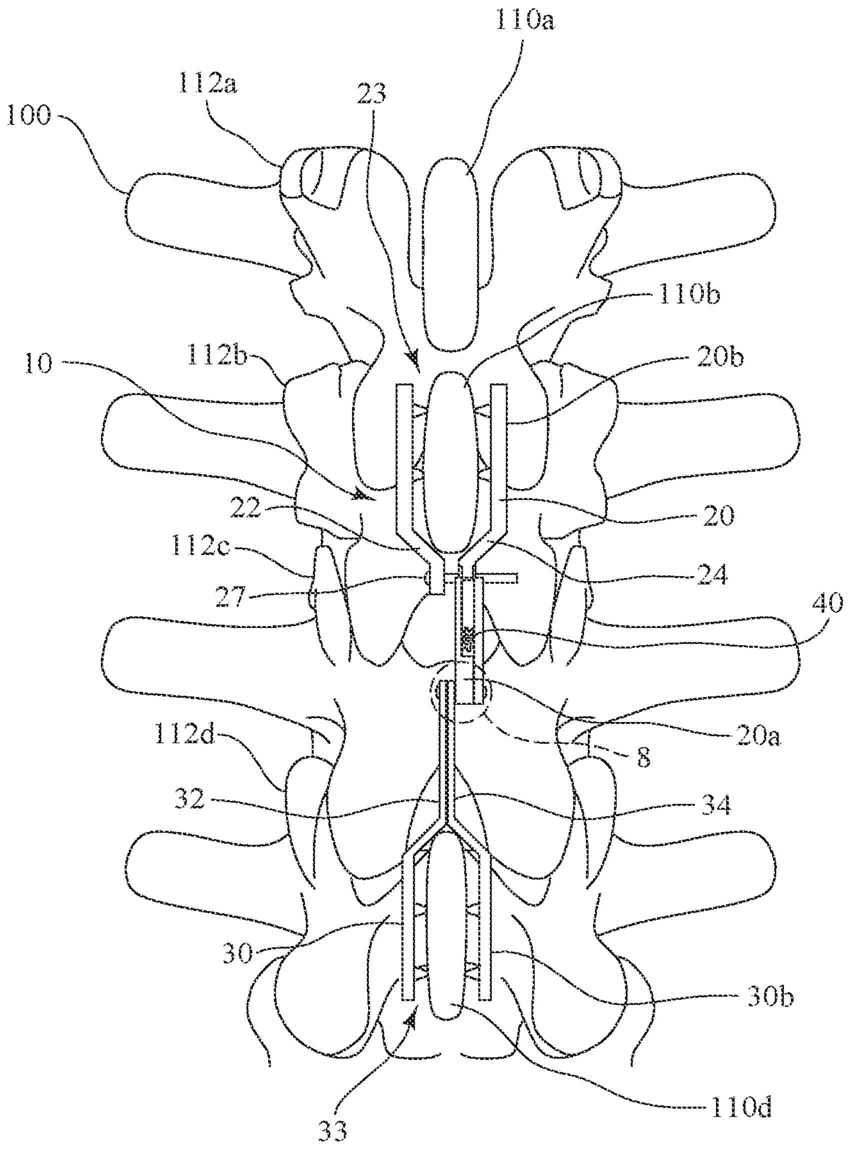
FIG. 1 is a view of an exemplary lumbar process static and dynamic stabilization device made in accordance with the present invention and affixed to two spinous processes of a lumbar spine.

FIG. 1 is a view of an exemplary lumbar process static and dynamic stabilization device 10 (or device 10) made in accordance with the present invention.

Figure 1A:
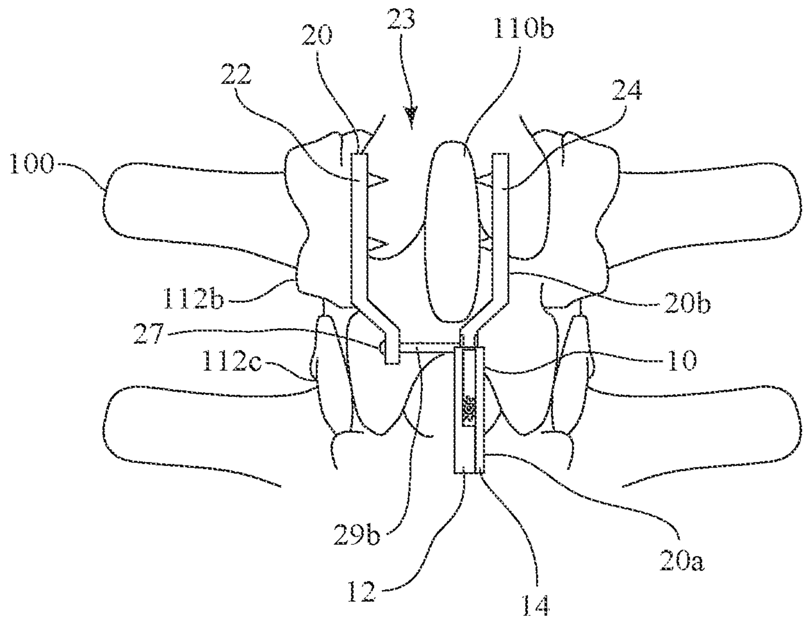
FIG. 1A is a partial view of the lumbar spine and the exemplary lumbar process static and dynamic stabilization device of FIG. 1, with the cavity of the upper arm of the device in a widened configuration.

FIG. 1A is a partial view of the lumbar spine and the exemplary lumbar process static and dynamic stabilization device 10 of FIG. 1, with a cavity 23 of the upper arm 20 of the device 10 in a widened configuration, as further described below.

Referring now to FIG. 1, an exemplary lumbar process static and dynamic stabilization device 10 made in accordance with the present invention is affixed to two spinous processes 110*b*, 110*d* of a lumbar spine 100, which includes a first vertebrae 112*a*, a second vertebrae 112*b*, a third vertebrae 112*c*, and a fourth vertebrae 112*d*. In this particular implementation, a laminectomy has been performed on the third vertebrae 112*c*, such that the spinous process corresponding to the third vertebrae 112*c* has been removed. The device 10 has been affixed to the spinous process 110*b* corresponding to the second vertebrae 112*b* and the spinous process 110*d* corresponding to the fourth vertebrae 112*d* to provide a support construct spanning between the second vertebrae 112*b* and the fourth vertebrae 112*d*. Accordingly, in this particular implementation, the device 10 thus spans across multiple vertebrae interspaces (i.e., the space between the second vertebrae 112*b* and the third vertebrae 112*c* and the space between the third vertebrae 112*c* and the fourth vertebrae 112*d*). It is appreciated, however, that the exhibited length of the device 10 can be adjusted to provide a construct extending between the spinous processes of two directly adjacent vertebrae (e.g., between the spinous process 110*a* corresponding to the first vertebrae 112*a* and the spinous process 110*b* corresponding to the second vertebrae 112*b*), and thus only span a single vertebrae interspace. In this regard, it is thus contemplated that, in some implementations, the device 10 may be utilized for a spinal support even in non-laminectomy-based procedures or spines on which a laminectomy has not been performed.

Figure 2A:
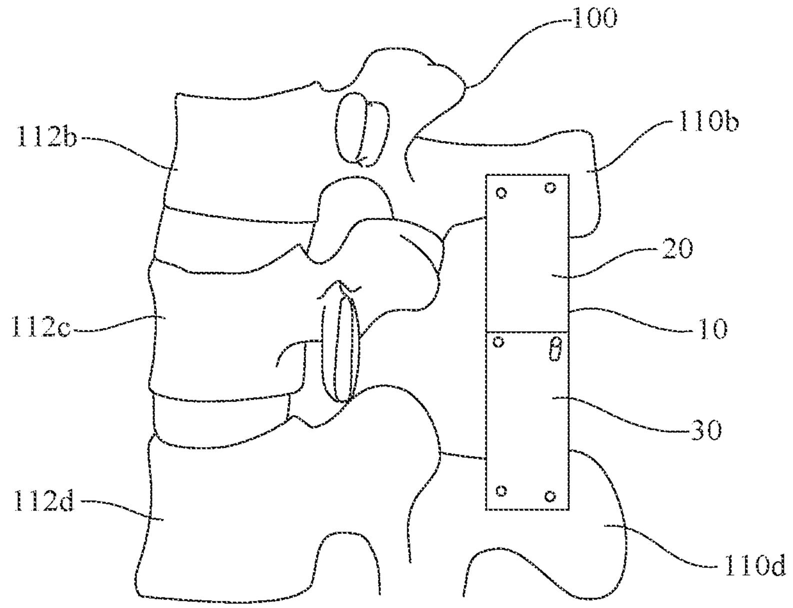
FIG. 2A is a schematic representation of the exemplary lumbar process static and dynamic stabilization device of FIG. 1.

FIG. 2A is a partial side view of the lumbar spine 100 of FIG. 1, with a schematic representation of the device 10 affixed to two spinous processes 110*b*, 110*d* and in a straightened orientation.

Figure 2B:
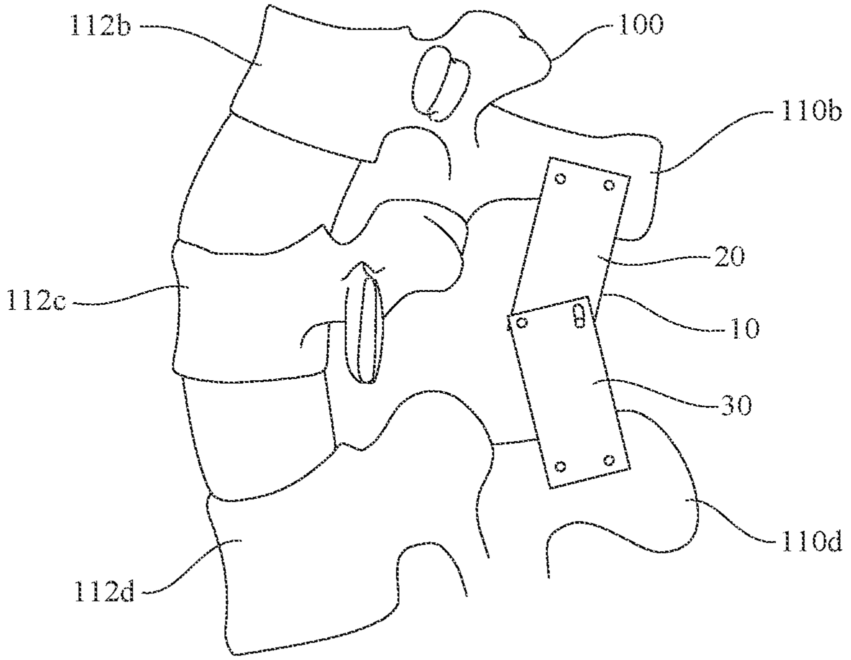
FIG. 2B is another schematic representation of the exemplary lumbar process static and dynamic stabilization device of FIG. 1.

FIG. 2B is a partial side view of the lumbar spine 100 similar to FIG. 2A, but with the schematic representation of the device 10 in an articulated orientation.

Referring now to FIGS. 1, 2A, and 2B, the device 10 generally includes an upper arm 20 configured to be affixed to a first spinous process of one vertebrae and a lower arm 30 configured to be affixed to a second spinous process of another vertebrae. As shown best in FIGS. 2A and 2B, the upper arm 20 and the lower arm 30 are pivotally connected, such that the upper arm 20 and the lower arm 30 can pivot relative to each other to transition the device 10 to a desired orientation, for example, a straightened orientation as shown in FIG. 2A or an articulated orientation as shown in FIG. 2B. As further described below, the device 10 can be selectively locked into either a static configuration by a locking mechanism or allowed to move dynamically, such that the upper arm 20 and the lower arm 30 of the device 10 are allowed to move relative to each other in response to manipulation of the portion of the lumbar spine 100 on which the device 10 is implemented. The device 10 of the present invention can thus function as either a fixed-angle or variable angle construct, such that it can be utilized in fusion-based applications or settings (e.g., to supplement anterior instrumentation during lumbar fusion) and non-fusion-based applications or settings alike.

Figure 3:
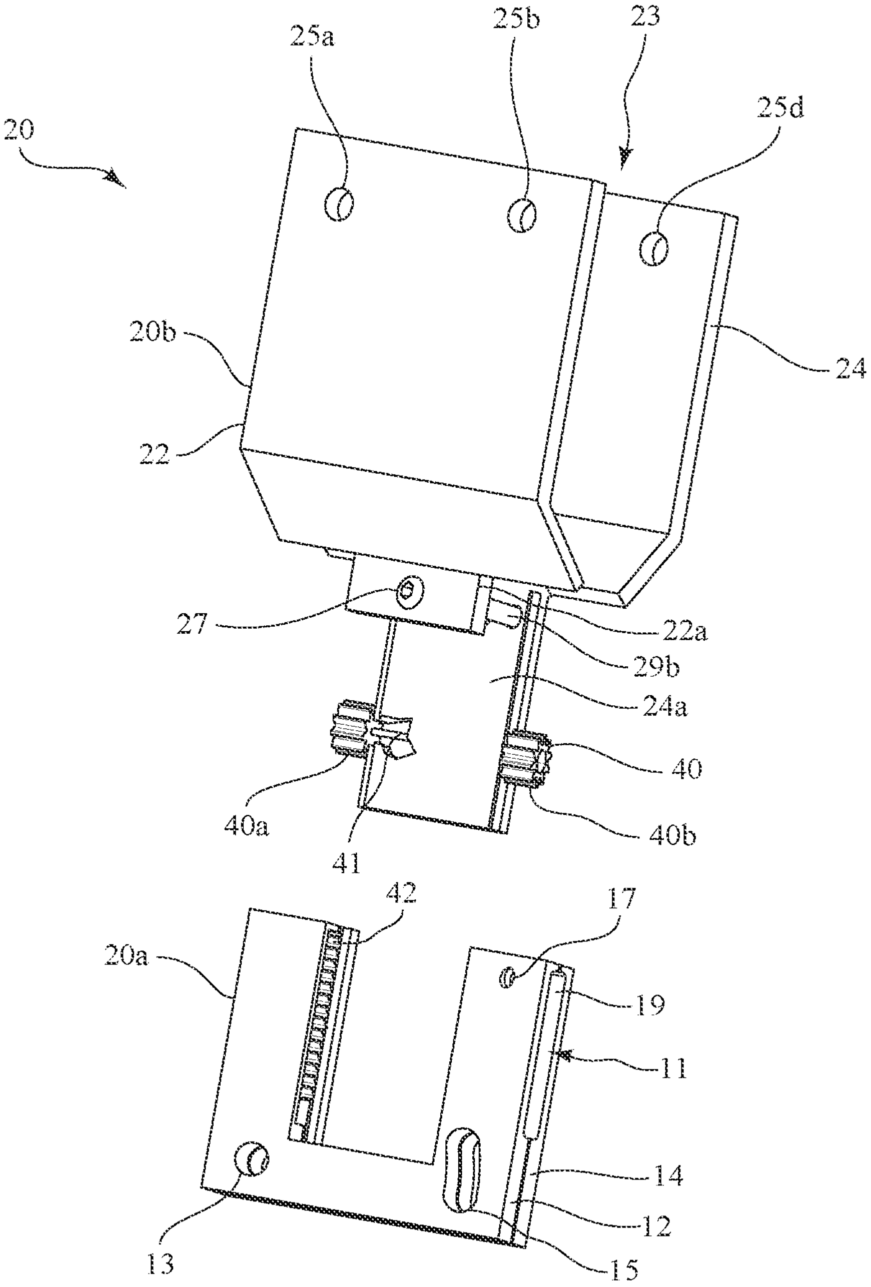
FIG. 3 is a perspective view of the upper arm of the exemplary lumbar process static and dynamic stabilization device of FIG. 1, with a base of the upper arm disassociated from a brace of the upper arm.

FIG. 3 is a perspective view of the upper arm 20 of the device 10 of FIG. 1, with a base 20*a* of the upper arm 20 disassociated from a brace 20*b* of the upper arm 20.

Figure 4:
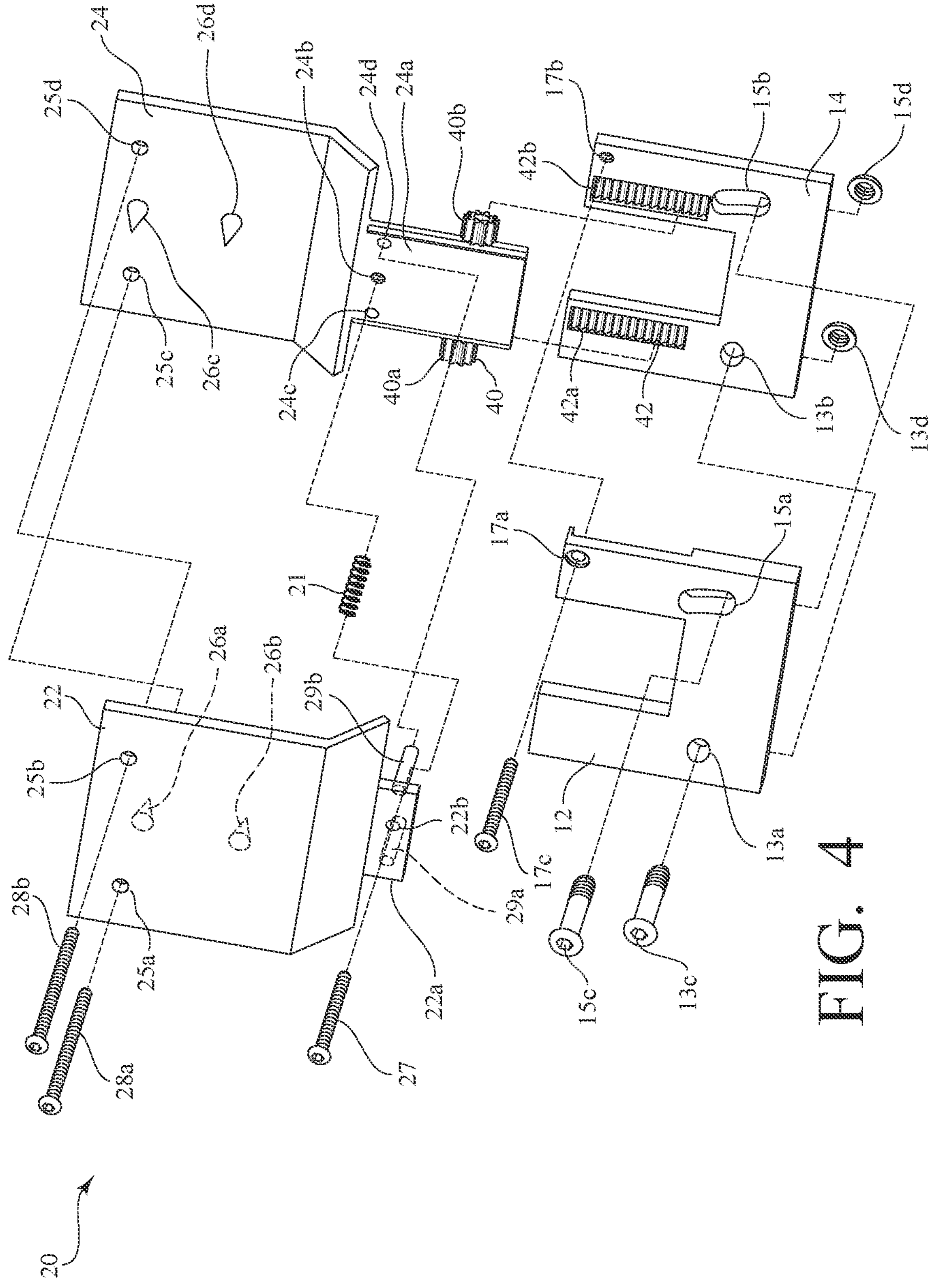
FIG. 4 is an exploded perspective view of the upper arm of the exemplary lumbar process static and dynamic stabilization device of FIG. 1.

FIG. 4 is an exploded perspective view of the upper arm 20 of the device of FIG. 1.

Figure 5A:
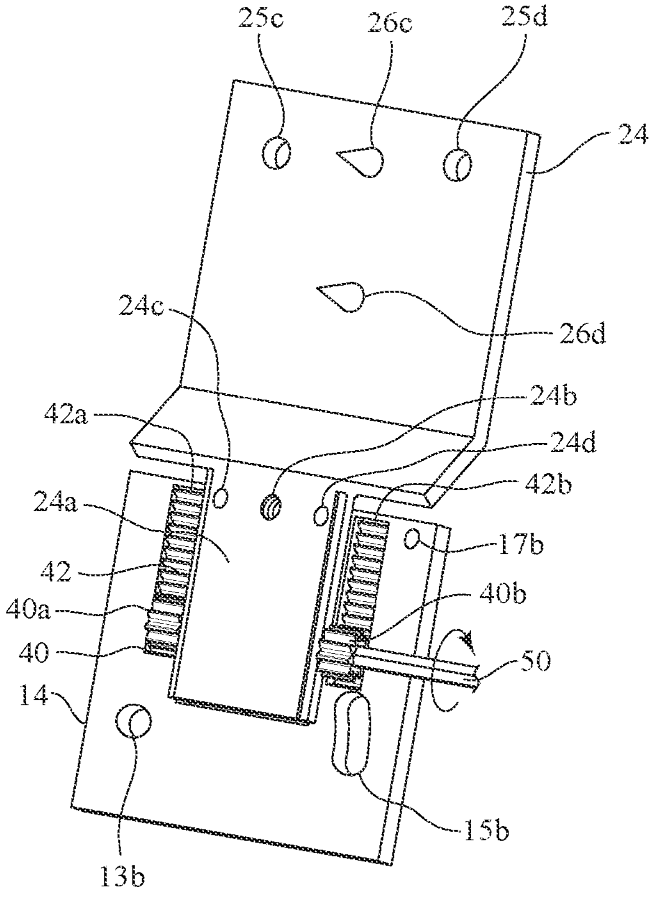
FIG. 5A is a partial view of the upper arm of the exemplary lumbar process static and dynamic stabilization device of FIG. 1, with the brace of the upper arm in a first (or lowered) position.

FIG. 5A is a partial view of the upper arm 20 of the device of FIG. 1, with the brace 20*b* of the upper arm 20 in a first (or lowered) position.

Figure 5B:
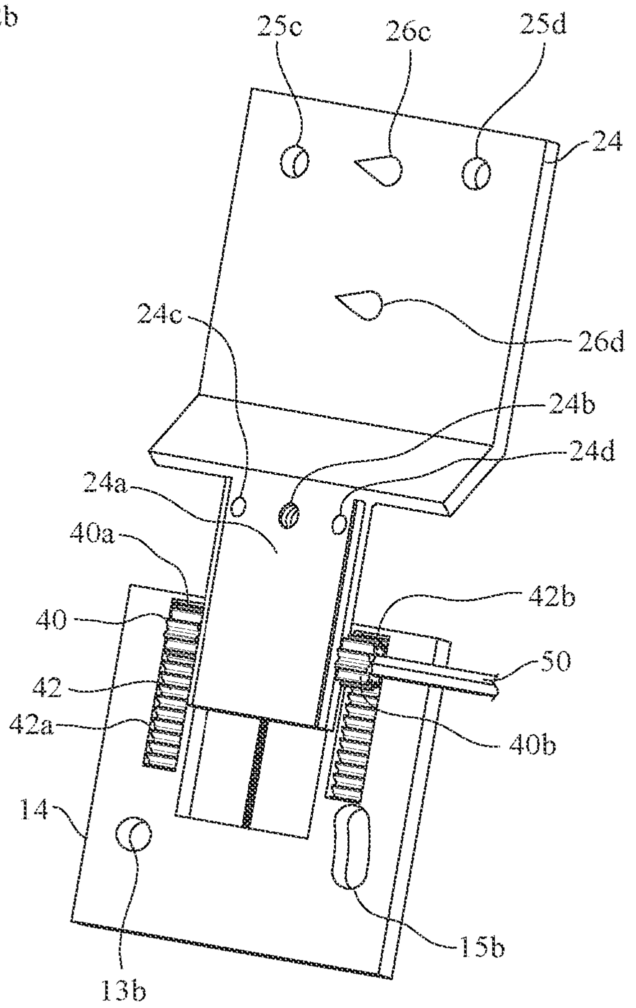
FIG. 5B is another partial view of the upper arm of the exemplary lumbar process static and dynamic stabilization device of FIG. 1, with the brace of the upper arm in a second (or raised) position.

FIG. 5B is a partial view of the upper arm 20 similar to FIG. 5A, but with the brace 20*b* of the upper arm 20 in a second (or raised) position.

Referring now to FIGS. 1, 1A, 3, 4, 5A, and 5B, the upper arm 20 can be characterized as including: the base 20*a*, which is secured to the lower arm 30; and the brace 20*b*, which is configured to receive and be affixed to a first target spinous process, which, in this example (FIGS. 1, 1A, 2A, and 2B), is the spinous process 110*b* corresponding to the second vertebrae 112*b* of the lumbar spine 100. In this regard, the brace 20*b* of the upper arm 20 has a shape similar to that of a stirrup, with a first side portion 22 and the second side portion 24 which define a cavity 23 in which the first spinous process is received.

Referring still to FIGS. 1, 1A, 3, 4, 5A, and 5B, in this exemplary embodiment, the first side portion 22 and second side portion 24 define a first pair of openings 25*a*, 25*b* and a second pair of openings 25*c*, 25*d*, respectively. The first pair of openings 25*a*, 25*b* and the second pair of openings 25*c*, 25*d* are aligned so that screws 28*a*, 28*b*, such as bicortical or unicortical screws, can be inserted as necessary through the first side portion 22 and/or the second side portion 24 to secure the first spinous process in the cavity 23 of the brace 20*b* of the upper arm 20. (Such screws 28*a*, 28*b* are not shown in FIGS. 1, 1A, 2, and 3.) As shown in FIGS. 1, 1A, 4, 5A, and 5B, in this exemplary embodiment, the interior surfaces of the first and second side portions 22, 24 of the brace 20*b* are also provided with bone spikes 26*a*, 26*b*, 26*c*, 26*d* to further assist in securing the brace 20*b* of the upper arm 20 to the first spinous process.

Referring still to FIGS. 1, 1A, 3, 4, 5A, and 5B, the first side portion 22 of the brace 20*b* includes a bracket 22*a* that extends downwardly from the portion of the first side portion 22, which again engages the first spinous process when the device 10 is in use. The second side portion 24 of the brace 20*b* includes a tongue 24*a*, which, like the bracket 22*a* of the first side portion 22, extends downwardly from the portion of the second side portion 24 that engages the first spinous process when the device 10 is in use. In this exemplary embodiment, the tongue 24*a* defined by the second side portion 24 is, however, more pronounced (i.e., longer) than the bracket 22*a* defined by the first side portion 22 of the brace 20*b*. The bracket 22*a* defines an opening 22*b*, and the tongue 24*a* defines a corresponding threaded opening 24*b*. A threaded fastener 27 can thus be inserted through the opening 22*b* defined by the bracket 22*a* and then into the threaded opening 24*b* defined by the second side portion 24.

Referring now specifically to FIG. 4, in this exemplary embodiment, the device 10 includes a spring 21 that is positioned between the first side portion 22 and the second side portion 24 of the brace 20*b* of the upper arm 20, with the fastener 27 passing through a central channel defined by the spring 21. The spring 21 provides a biasing force between the first side portion 22 and the second side portion 24. Furthermore, to maintain the first side portion 22 and the second side portion 24 in alignment with one another, in this exemplary embodiment, the device 10 further includes a first pin 29*a* and a second pin 29*b*. The first pin 29*a* extends from the bracket 22*a* and into an opening 24*c* defined by the tongue 24*a*. Similarly, the second pin 29*b* extends from the bracket 22*a* and into another opening 24*d* defined by the tongue 24*a*.

Referring now to FIGS. 1, 1A, and 4, in this exemplary embodiment, the fastener 27 securing the first side portion 22 to the second side portion 24 of the brace 20*b* of the upper arm 20 can be rotated (i.e., tightened or loosened) to reposition the first side portion 22 relative to the second side portion 24. In this regard, if the fastener is loosened, the spring 21 will push the first side portion 22 away from the second side portion 24. In this way, the distance between the first side portion 22 and the second side portion 24 can be adjusted. Thus, the cavity 23 defined by the brace 20*b* of the upper arm 20 can be widened or narrowed to accommodate spinal processes of different dimensions.

Referring now to FIGS. 3 and 4, the base 20*a* of the upper arm 20 includes a first base plate 12 and a second base plate 14. In this exemplary embodiment, when combined, the first base plate 12 and the second base plate 14 collectively define an interior cavity 11, as further described below. In this exemplary embodiment, and as best shown in FIG. 3, the first base plate 12 and the second base plate 14 also collectively define a first opening 13, a second opening 15, and a third opening 17. As best shown in FIG. 4, the first opening 13 is defined by a hole 13*a* defined by the first base plate 12 and a corresponding hole 13*b* defined by the second base plate 14. The second opening 15 is defined by an elongated slot 15*a* defined by the first base plate 12 and a corresponding elongated slot 15*b* defined by the second base plate 14. The third opening 17 is defined by a hole 17*a* defined by the first base plate 12 and a corresponding hole 17*b* defined by the second base plate 14. The function and use of these openings 13, 15, 17 will be further described below.

Now, as shown by viewing FIGS. 5A and 5B, in sequence, the tongue 24*a* (and thus the brace 20*b* as a whole) of the upper arm 20 is configured for movement with respect to the base 20*a* of the upper arm 20, such that that the brace 20*b* can be selectively raised or lowered to adjust the length of the upper arm 20, and, thus, the overall length of the device 10. In this way, the length of the device 10 can be selectively adjusted to span across one or more vertebrae interspaces to engage two target spinous processes, as further described below.

Referring now again to FIGS. 1, 3, 4, 5A, and 5B, in this exemplary embodiment, movement of the brace 20*b* relative to the base 20*a* of the upper arm 20 is accomplished by a rack-and-pinion arrangement. In this regard, the upper arm 20 includes a pinion 40 extending through and mounted for rotation with respect to the tongue 24*a*. The upper arm 20 further includes a rack 42 with a plurality of notches with which the pinion 40 can engage to reposition the brace 20*b* relative to the base 20*a* of the upper arm 20. In this exemplary embodiment, the rack 42 is defined by an interior surface of the second base plate 14 of the base 20*a* of the upper arm 20. As such, in use, the pinion 40 is effectively housed within the cavity 11 defined by the first base plate 12 and the second base plate 14 of the base 20*a* of the upper arm 20, where it engages the rack 42.

Figure 6A:
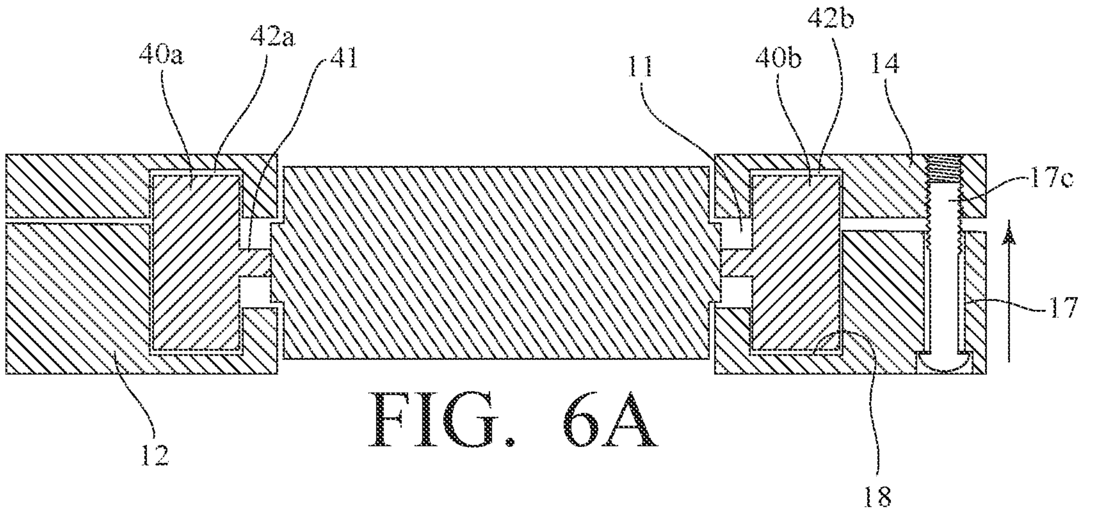
FIG. 6A is a sectional view of the upper arm of the exemplary lumbar process static and dynamic stabilization device of FIG. 1.
Figure 6B:
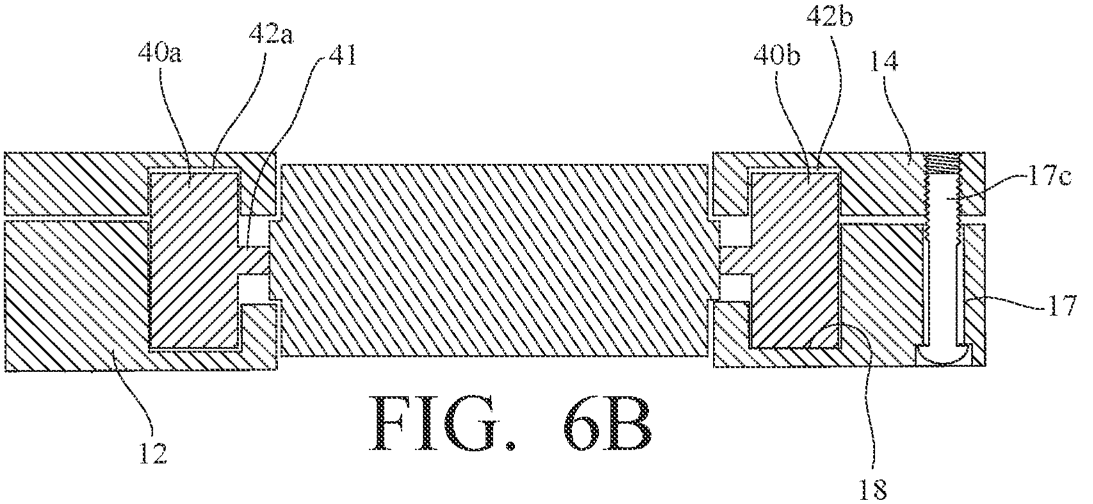
FIG. 6B is another sectional view of the upper arm of the exemplary lumbar process static and dynamic stabilization device of FIG. 1.

As best shown in FIGS. 3, 4, 5A, and 5B, in this exemplary embodiment, the pinion 40 includes a first head 40*a* and a second head 40*b*, which are mounted on opposing sides of the tongue 24*a*. The first head 40*a* of the pinion 40 engages a first track 42*a* of the rack 42, and the second head 40*b* of the pinion 40 engages a second track 42*b* of the rack 42. The first head 40*a* and the second head 40*b* of the pinion 40 are connected by an axle 41 (as shown in FIGS. 3, 6A, and 6B), such that, as one head of the pinion 40 is rotated, the other head simultaneously rotates. To drive rotation of the pinion 40, one or both of the first and second heads 40*a*, 40*b* are configured to receive a tool 50. As shown in FIGS. 5A and 5B, once engaged with the pinion 40, the tool 50 can be rotated to rotate the pinion 40 and move it along the first track 42*a* and second track 42*b* of the rack 42. To enable the tool 50 to access the pinion 40, the first base plate 12 and the second base plate 14 collectively define an access channel 19, as best shown in FIG. 3, which permits the tool 50 to be inserted into the cavity 11 defined by the first base plate 12 and the second base plate 14 of the base 20*a*.

FIG. 6A is a sectional view of the upper arm 20 of the device 10 of FIG. 1, taken just above a fastener 17*c* within the third opening 17, with the base 20*a* of the upper arm 20 in a first configuration which permits movement of the pinion 40 along the rack 42.

FIG. 6B is a sectional view similar to that of FIG. 6A, but with the fastener 17*c* further tightened to reduce the spacing between the first base plate 12 and the second base plate 14, thus causing the base 20*a* of the upper arm 20 to retain a second configuration which prevents movement of the pinion 40.

Referring now to FIGS. 6A and 6B, once the upper arm 20 has been set to the desired length, the positioning of the pinion 40 along the rack 42 can be locked into place to maintain the upper arm 20 at the desired length. In this regard, the upper arm 20 thus also includes a locking mechanism, which can be selectively engaged to allow or prevent movement of the pinion 40 along the rack 42. In this exemplary embodiment, the locking mechanism is effectively defined by the first base plate 12, the second base plate 14, and the fastener 17*c*. Specifically, in this exemplary embodiment, a compressive force can be applied to the pinion 40 by tightening the fastener 17*c* received in the third opening 17 defined by the first base plate 12 and the second base plate 14. As shown by viewing FIGS. 6A and 6B, in sequence, as the fastener 17*c* is tightened, the first base plate 12 and the second base plate 14 are drawn closer to each other, thereby closing a space 18 within the cavity 11 and clamping onto the first head 40*a* and/or second head 40*b* of the pinion 40, thus restricting movement of the pinion 40. Accordingly, in this exemplary embodiment, the base 20*a* of the upper arm 20 can thus be transitioned between (i) a first (or open) configuration (FIG. 6A) that permits movement of the pinion 40 along the rack 42, and (ii) a second (or locked) configuration (FIG. 6B) that prevents movement of the pinion 40 along the rack 42. In use, the base 20*a* of the upper arm 20 can be left in the first (open) configuration to permit compression and distraction of vertebrae. In such an implementation, the locking mechanism defined by the first base plate 12, the second base plate 14, and fastener 17*c* can thus be characterized as being in a "disengaged" or "unlocked" configuration.

Figure 7:
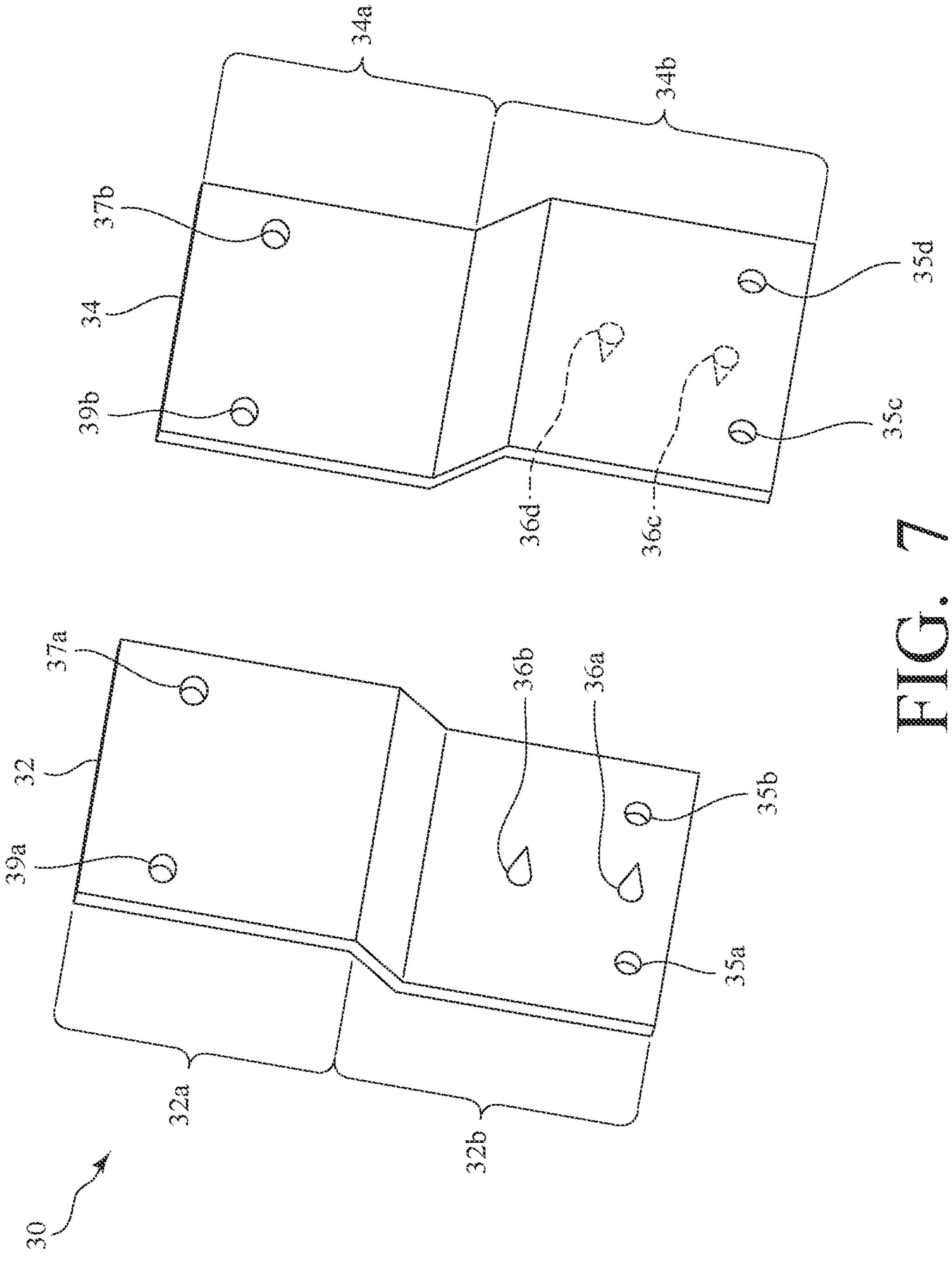
FIG. 7 is perspective view of a lower arm of the exemplary lumbar process static and dynamic stabilization device of FIG. 1, with a first side portion of the lower arm disassociated from a second side portion of the lower arm.

FIG. 7 is a perspective view of the lower arm 30 of the device 10 of FIG. 1, with a first side portion 32 of the lower arm 30 disassociated from a second side portion 34 of the lower arm 30.

Referring now to FIGS. 1 and 7, in this exemplary embodiment, the lower arm of the device 10 is defined by, and thus can be characterized as including, the first side portion 32 and the second side portion 34. The first side portion 32 and the second side portion 34 each include an upper section 32*a*, 34*a* and a lower section 32*b*, 34*b*. When combined, the respective lower sections 32*b*, 34*b* of the first side portion 32 and the second side portion 34 collectively define a brace 30*a*, which is configured to receive and be affixed to a second target spinous process, which, in this example (FIGS. 1, 1A, 2A, and 2B), is the spinous process 110*d* corresponding to the fourth vertebrae 112*d*. Thus, like the brace 20*b* of the upper arm 20, the brace 30*a* of the lower arm 30 also has a shape similar to that of a stirrup. In this regard, the respective lower sections 32*b*, 34*b* of the first side portion 32 and the second side portion 34 also define a cavity 33 in which the second target spinous process is received. When combined, the respective upper sections 32*a*, 34*a* of the first side portion 32 and the second side portion 34 define a base which can be secured to the base 20*a* of upper arm 20. In this exemplary embodiment, the upper section 32*a* and the lower section 32*b* of the first side portion 32 are integrally formed, and the upper section 34*a* and the lower section 34*b* of the second side portion 34 are also integrally formed. Thus, in this exemplary embodiment, the brace 30*a* of the lower arm 30 is not configured for movement with respect to the base of the lower arm 30 (unlike the upper arm 20).

Referring still to FIGS. 1 and 7, in this exemplary embodiment, the lower section 32*b* of the first side portion 32 defines a first pair of holes 35*a*, 35*b*, and the lower section 34*b* of the second side portion 34 defines a second pair of holes 35*c*, 35*d*. In use, the first pair of holes 35*a*, 35*b* and the second pair of holes 35*c*, 35*d* are aligned, so that screws (not shown), such as bicortical or unicortical screws, can be inserted through the first side portion 32 and/or the second side portion 34 as necessary to secure the second spinous process in the cavity 33 of the brace 30*a* of the lower arm 30. In this exemplary embodiment, the interior surfaces of the first and second side portions 32, 34 of the brace 30*a* are also provided with bone spikes 36*a*, 36*b*, 36*c*, 36*d* to further assist in securing the brace 30*a* of the lower arm 30 to the second spinous process.

Referring now specifically to FIG. 7, in this exemplary embodiment, the upper section 32*a* of the first side portion 32 of the lower arm 30 defines a first hole 37*a* and a second hole 39*a*. The upper section 34*a* of the second side portion 34 of the lower arm 30 similarly defines a first hole 37*b* and a second hole 39*b*. When the first side portion 32 and the second side portion 34 of the lower arm 30 are combined, the first holes 37*a*, 37*b* collectively define a first opening corresponding to the first opening 13 of the upper arm 20, and the second holes 39*a*, 39*b* collectively define a second opening corresponding to the second opening 15 of the upper arm 20.

Figure 8:
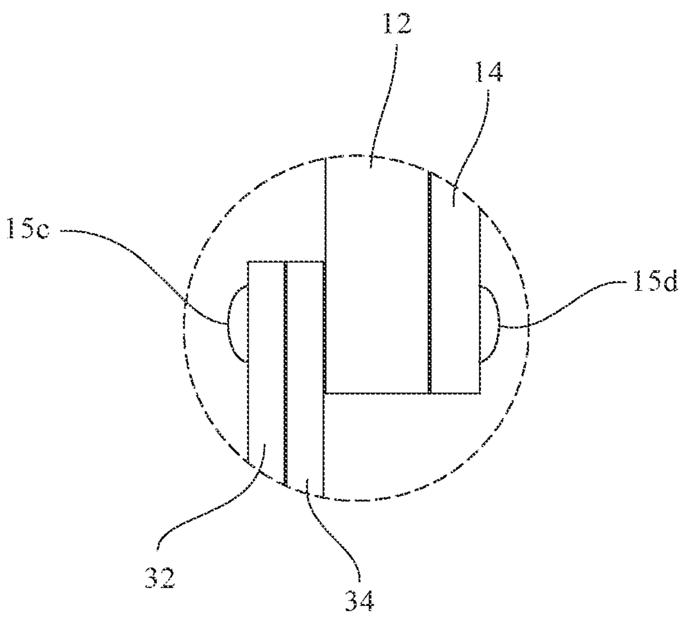
FIG. 8 is an enlarged view of a connection between the upper arm and the lower arm of the exemplary lumbar process static and dynamic stabilization device of FIG. 1.

FIG. 8 is an enlarged view of the connection between the upper arm 20 and the lower arm 30.

Referring now to FIGS. 1, 3, 4, 7, and 8, the upper arm 20 and the lower arm 30 are secured together by aligning the first opening 13 of the upper arm 20 with the opening defined by the first holes 37*a*, 37*b* of the first and second side portions 32, 34 of the lower arm 30, and then inserting a fastener 13*c* therethrough, which, in this exemplary embodiment, then engages and is secured by a nut 13*d*. Furthermore, in this exemplary embodiment, the holes 13*a*, 13*b* of the first opening 13 of the upper arm 20 and the holes 37*a*, 37*b* of the first and second side portions 32, 34 of the lower arm 30 are each common round holes that receive the fastener 13*c*, thus creating a pivot connection which enables the upper arm 20 and the lower arm 30 to move relative to each other about an axis defined by the fastener 13*c*. Such a pivot connection permits the device 10 to transition to a desired orientation, for example, a straightened orientation as shown in FIG. 2A or an articulated orientation as shown in FIG. 2B.

Referring still to FIGS. 1, 3, 4, 7, and 8, the upper arm 20 and the lower arm 30 are further secured together by aligning the second opening 15 of the upper arm 20 with the opening defined by the second holes 39*a*, 39*b* of the first and second side portions 32, 34 of the lower arm 30, and inserting a fastener 15*c* therethrough, which, in this exemplary embodiment, then engages and is secured by a nut 15*d*. Furthermore, in this exemplary embodiment, the second opening 15 of the upper arm 20 is defined by an elongated slot 15*a* defined by the first base plate 12 and a corresponding elongated slot 15*b* defined by the second base plate 14, while the corresponding holes 39*a*, 39*b* defined by the first and second side portions 32, 34 of the lower arm 30 are common round holes. In this regard, the shape of the second opening 15 of the upper arm 20 thus defines a range in which the upper arm 20 and the lower arm 30 can move relative to each other via the pivot connection formed by insertion of the fastener 13*c* through the first opening 13 of the upper arm 20 and the opening defined by the first holes 37*a*, 37*b* of the first and second side portions 32, 34 of the lower arm 30.

In some embodiments, the device 10 includes a locking mechanism for securing the lower arm 30 in a desired orientation relative to the upper arm 20. In other words, the device 10 can be placed in a "locked" configuration to maintain it in any desired orientation permitted by the pivot connection described above and the second opening 15, which again define the range in which the upper arm 20 and the lower arm 30 can pivot relative to each other. For example, in some implementations, the device 10 could be placed in a locked configuration to maintain the straightened orientation shown in FIG. 2A, while, in other implementations, the device 10 may be placed in a locked configuration to maintain an articulated orientation, such as that shown in FIG. 2B. To place the device in such a locked configuration, in some embodiments, the fastener 15*c* may be tightened to provide a compressive force that would draw the second side portion 34 of the lower arm 30 into engagement with the first base plate 12 of the upper arm 20, thus resisting any further pivoting of the lower arm 30 with respect to the upper arm 20.

Figure 9:
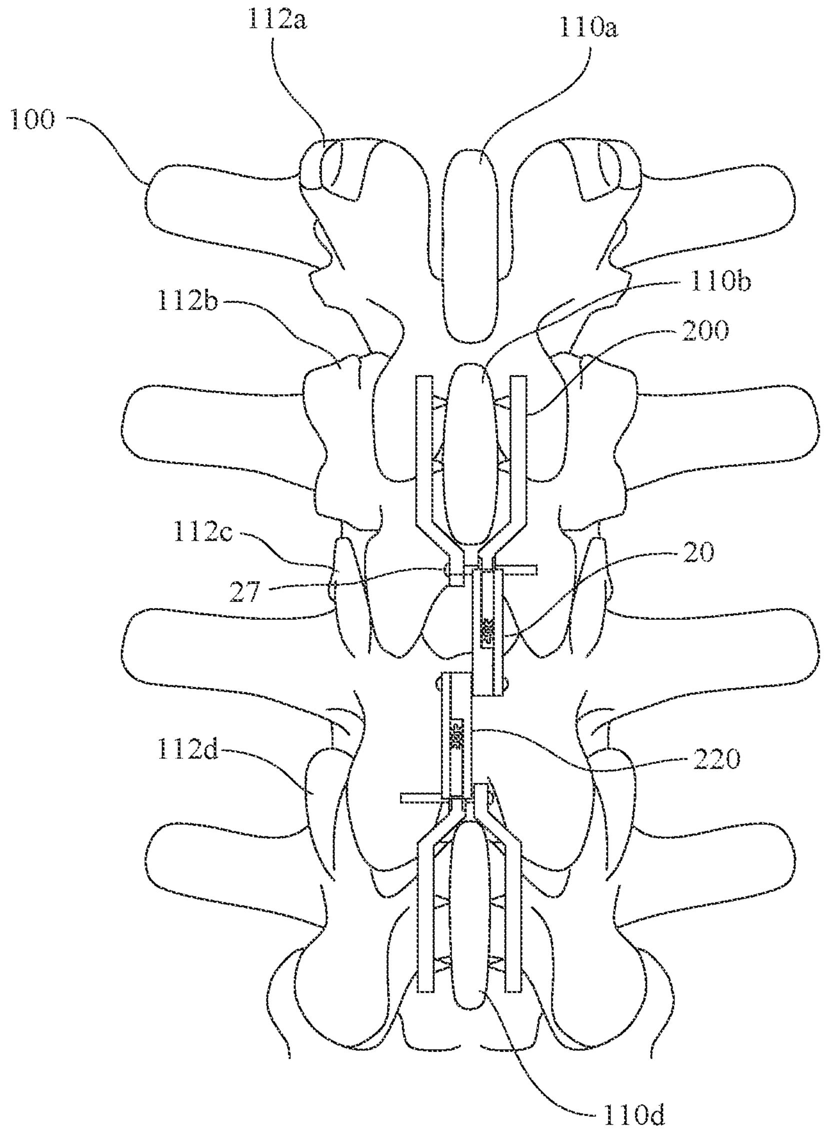
FIG. 9 is a view of another exemplary lumbar process static and dynamic stabilization device made in accordance with the present invention and affixed to two spinous processes of a lumbar spine.

FIG. 9 is a view of another exemplary lumbar process static and dynamic stabilization device 200 (or device 200) made in accordance with the present invention and affixed to two spinous processes 110*b*, 110*d* of a lumbar spine 100, which includes a first vertebrae 112*a*, a second vertebrae 112*b*, a third vertebrae 112*c*, and a fourth vertebrae 112*d*.

Figure 9A:
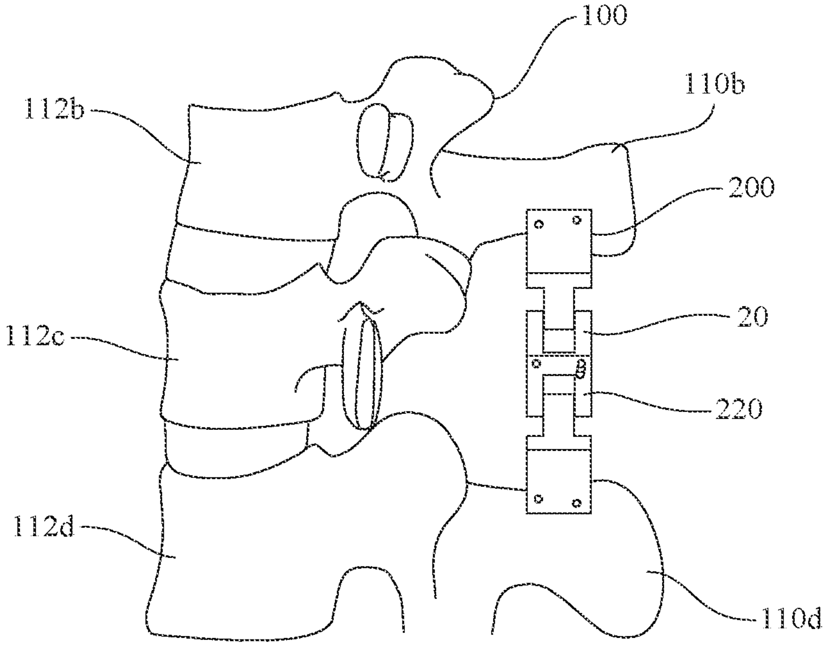
FIG. 9A is a schematic representation of the exemplary lumbar process static and dynamic stabilization device of FIG. 9.

FIG. 9A is a partial side view of the lumbar spine 100 of FIG. 9, with a schematic representation of the device 200 affixed to two spinous processes 110*b*, 110*d* and in a straightened orientation.

Figure 9B:
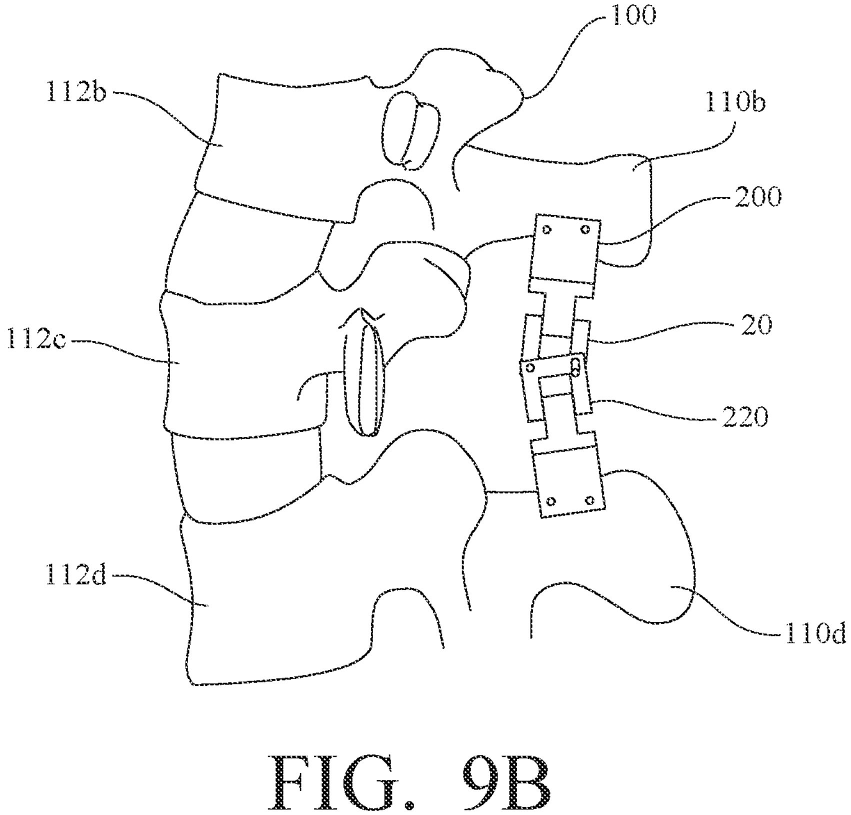
FIG. 9B is another schematic representation of the exemplary lumbar process static and dynamic stabilization device of FIG. 9.

FIG. 9B is a partial side view of the lumbar spine 100 similar to FIG. 9A, but with the schematic representation of the device 200 in an articulated orientation.

Referring now to FIGS. 9, 9A, and 9B, the static and dynamic stabilization device 200 shown in FIG. 9 includes the same upper arm 20 as the device 10 described above with respect to FIGS. 1, 2A, and 2B. The device 200 also includes a lower arm 220 pivotally connected to the upper arm 20, such that the upper arm 20 and the lower arm 220 can pivot relative to each other to transition the device 200 to a desired orientation. However, in this exemplary embodiment, the lower arm 220 is essentially identical to the upper arm 20, and thus includes the same structural features thereof, including the rack-and-pinion arrangement described above with reference to FIGS. 1, 3, 4, 5A, 5B, 6A, 6B, and 8. Thus, in this exemplary embodiment, the length of both the upper arm 20 and the lower arm 220 can be selectively adjusted by repositioning a pinion along a rack of the upper arm 20 and/or lower arm 220 to change the overall length of the device 200.

Figure 10:
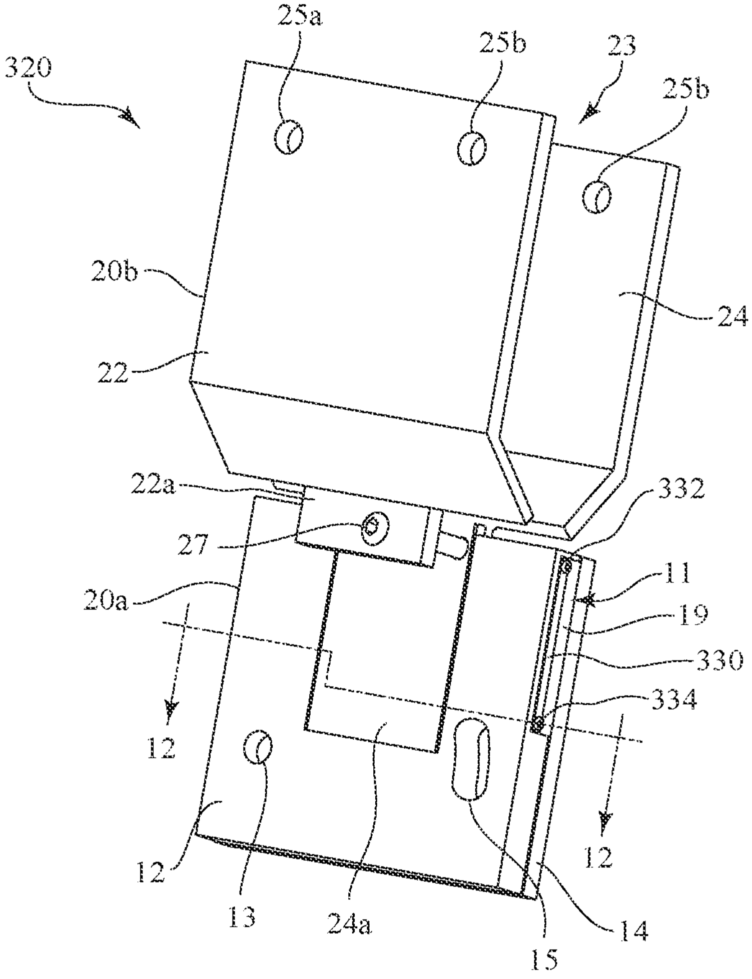
FIG. 10 is a perspective view of an alternate arm, which may be used in place of the upper arm and/or lower arm of the exemplary lumbar process static and dynamic stabilization devices of FIGS. 1 and 9.

FIG. 10 is a perspective view of an alternate arm 320, which may be used in place of the upper arm 20 and/or lower arm 30, 220 of the devices 10, 200 described above with reference to FIGS. 1, 2A, 2B, 9, 9A, and 9B.

Figure 11:
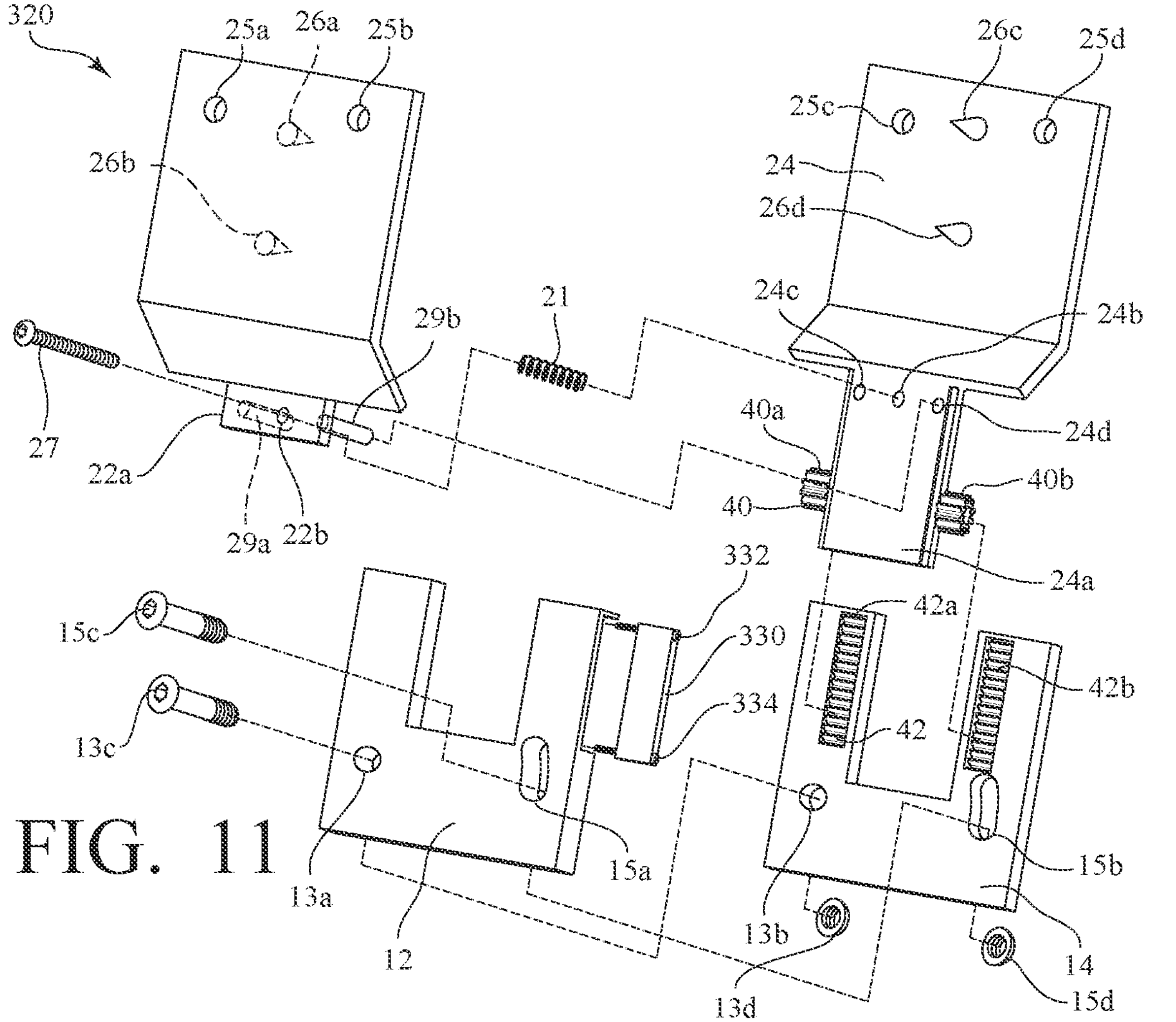
FIG. 11 is an exploded perspective view of the alternate arm of FIG. 10.

FIG. 11 is an exploded view of the alternate arm 320 of FIG. 10.

Figure 12:
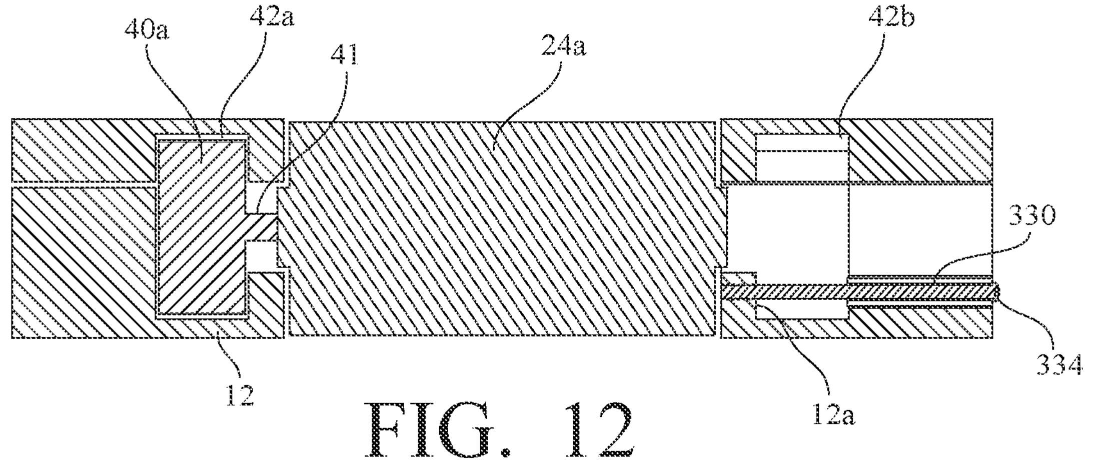
FIG. 12 is a sectional view of the alternate arm of FIG. 10, taken along line 12-12 of FIG. 10.

FIG. 12 is a sectional view of the alternate arm 320 of FIG. 10, taken along line 12-12 of FIG. 10.

Figure 13:
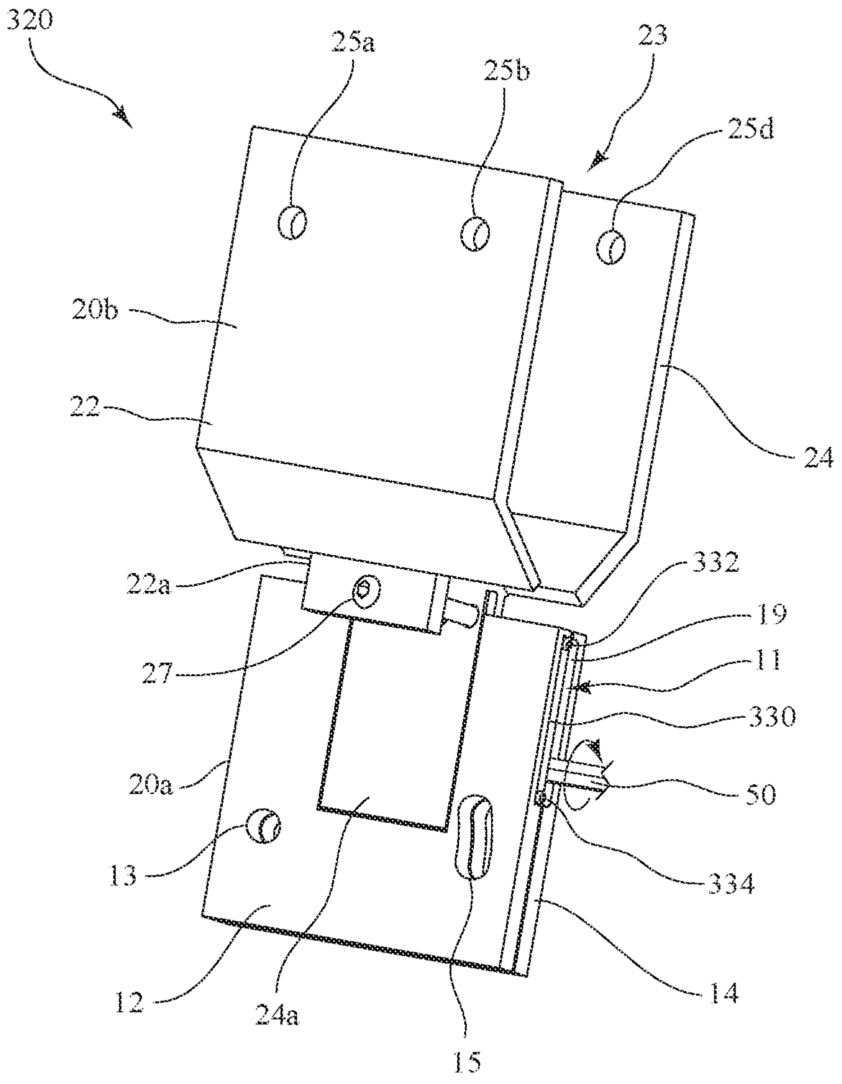
FIG. 13 is another perspective view of the alternate arm of FIG. 10.

FIG. 13 is another perspective view of the alternate arm 320 of FIG. 10.

Referring now to FIGS. 10-13, in this exemplary embodiment, the alternate arm 320 generally includes the same structural components and provides the same functionality as the upper arm 20 described above, except with regards to the locking mechanism that can be selectively engaged to maintain the alternate arm 320 at a desired length. Thus, like components are provided with the same reference numerals as provided above in describing the exemplary lumbar process static and dynamic stabilization devices 10, 200 of FIGS. 1, 2A, 2B, 9, 9A, and 9B.

Referring still to FIGS. 10-13, the alternate arm 320 includes the same pinion-and-rack arrangement as described above with respect to FIGS. 1, 3, 4, 5A, 5B, 6A, 6B, and 8. However, instead of drawing the first and second base plates 12, 14 together via the fastener 17*c* to clamp the pinion 40 against the rack 42, in this exemplary embodiment, the alternate arm 320 includes a plate 330 which acts as the locking mechanism. The plate 330 is positioned adjacent to an outer face of the second head 40*b* of the pinion 40 and can be drawn against the second head 40*b* of the pinion 40 by engaging (tightening) a first fastener 332 and a second fastener 334, which, in this exemplary embodiment, are screws that hold the plate 330 within the access channel 19 defined by the first and second base plates 12, 14 of the alternate arm 320. In this regard, there are threaded openings 12*a* (one of which is visible in FIG. 12) defined in an interior wall of the first base plate 12 to receive the first fastener 332 and the second fastener 334. The compressive force applied by virtue of the plate 330 being drawn against the second head 40*b* of the pinion 40 prevents subsequent movement of the pinion 40 along the rack 42. To permit engagement of the tool 50 with the second head 40*b* of the pinion 40, the plate 330 and corresponding fasteners 332, 334 are preferably offset from the center of the outer face of the second head 40*b* of the pinion 40, as best shown in FIGS. 12 and 13.

Figure 14:
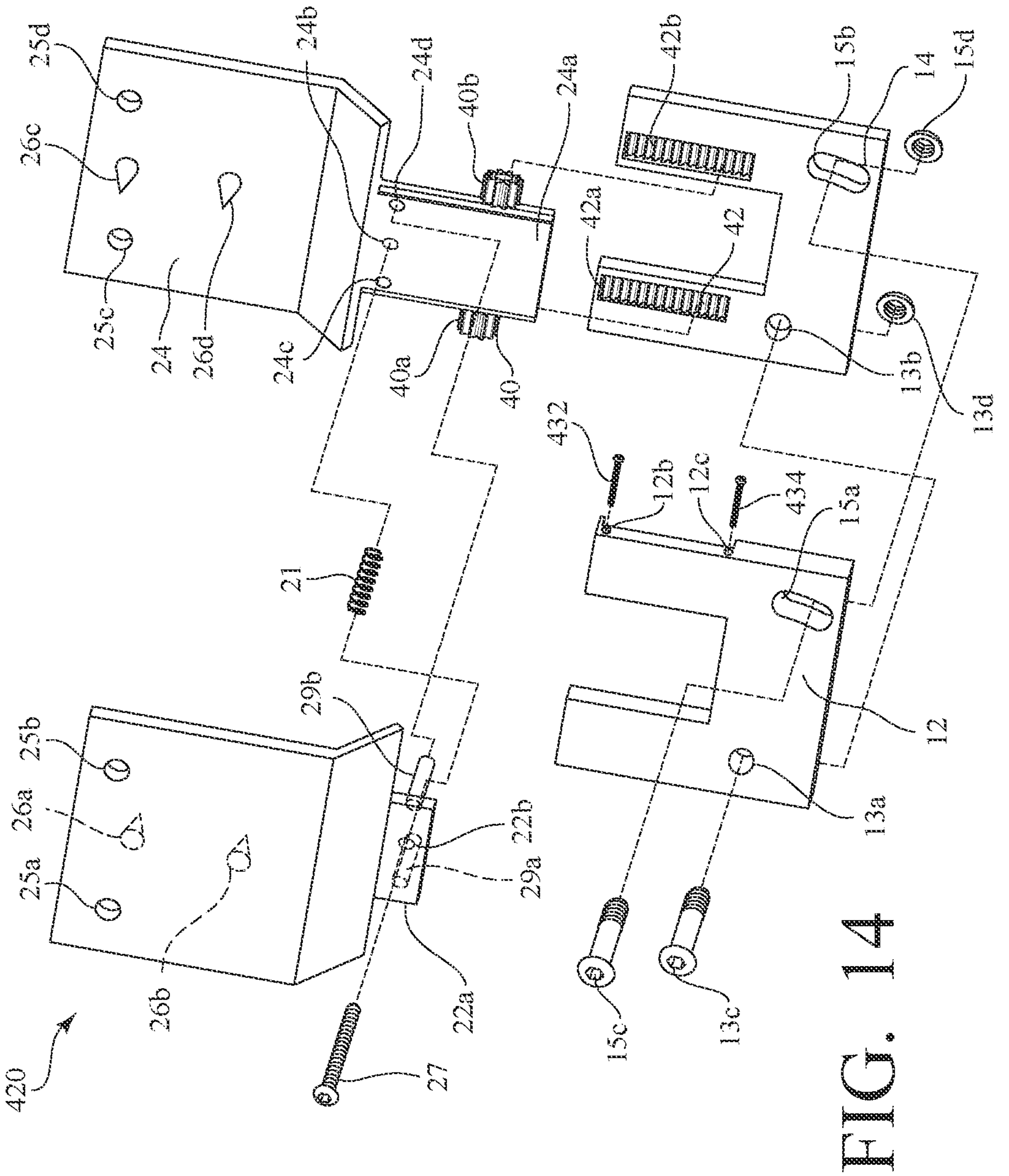
FIG. 14 is an exploded perspective view of another alternate arm, which may be used in place of the upper arm and/or lower arm of the exemplary lumbar process static and dynamic stabilization devices of FIGS. 1 and 9.

FIG. 14 is an exploded perspective view of another alternate arm 420, which may be used in place of the upper arm 20 and/or lower arm 30, 220 of the devices 10, 200 described above with reference to FIGS. 1, 2A, 2B, 9, 9A, and 9B.

Referring now to FIG. 14, in this exemplary embodiment, the alternate arm 420 generally includes the same structural components and provides the same functionality as the alternate arm 320 described above with reference to FIGS. 10-13, except with regards to the locking mechanism that can be selectively engaged to maintain the alternate arm 420 at a desired length. Thus, like components are provided with the same reference numerals as provided above in describing the alternate arm 320 of FIG. 10.

Referring still to FIG. 14, instead of drawing a plate against an outer face of the second head 40*b* of the pinion 40, in this exemplary embodiment, two fasteners 432, 434 (which, in this case, are screws) can be tightened to apply pressure to and push the tongue 24*a* to which the pinion 40 is mounted for rotation towards an interior wall within the cavity 11 defined by the first and second base plates 12, 14, which effectively moves the pinion 40 out of alignment with the rack 42, thus preventing movement of the pinion relative to the rack 42. In this exemplary embodiment, the first base plate 12 defines two threaded openings 12*b*, 12*c* which guide the two fasteners 432, 434 into the cavity 11 defined by the first base plate 12 and the second base plate 14.

Figure 15:
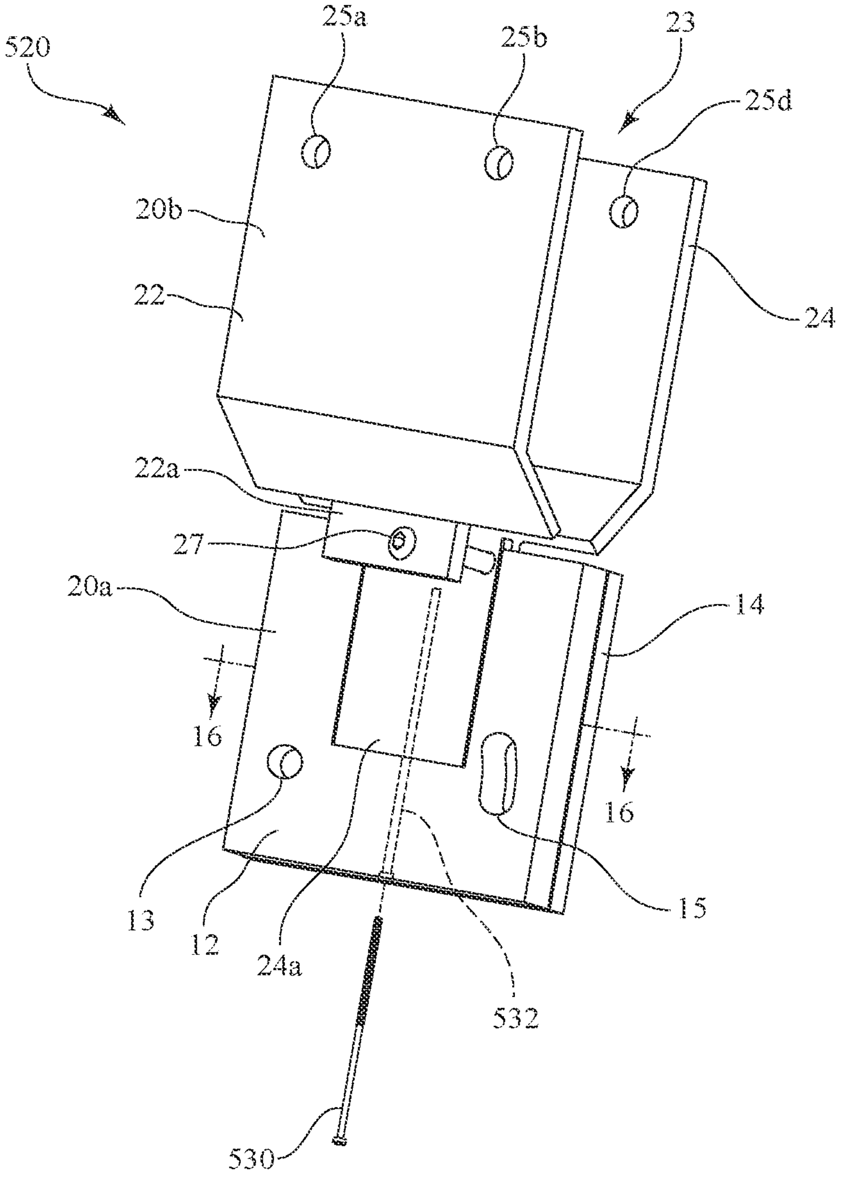
FIG. 15 is a perspective view of yet another alternate arm, which may be used in place of the upper arm and/or lower arm of the exemplary lumbar process static and dynamic stabilization devices of FIGS. 1 and 9.

FIG. 15 is a perspective view of another alternate arm 520, which may be used in place of the upper arm 20 and/or lower arm 30, 220 of the devices 10, 200 described above with reference to FIGS. 1, 2A, 2B, 9, 9A, and 9B.

Figure 16:
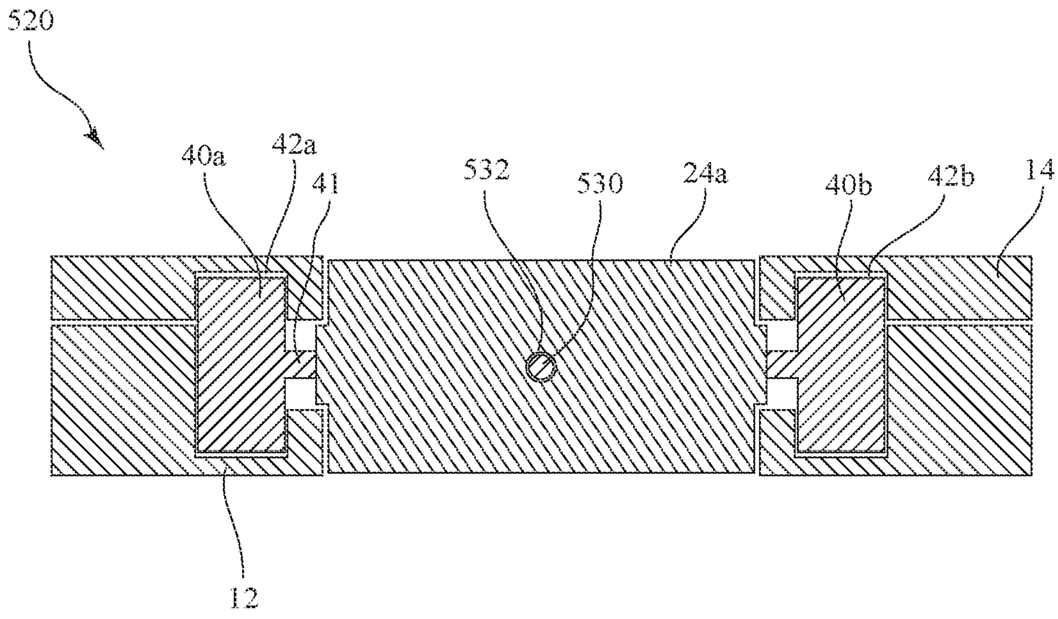
FIG. 16 is a sectional view of the arm of FIG. 15 taken along line 16-16 of FIG. 15.

FIG. 16 is a sectional view of the alternate arm 520 of FIG. 15 taken along line 16-16 of FIG. 15.

Referring now to FIGS. 15 and 16, in this exemplary embodiment, the alternate arm 520 generally includes the same structural components and provides the same functionality as the upper arm 20 described above, except with regards to the locking mechanism which can be selectively engaged to maintain the alternate arm 520 at a desired length. Thus, like components are provided with the same reference numerals as provided above in describing the exemplary lumbar process static and dynamic stabilization devices 10, 200 of FIGS. 1, 2A, 2B, 9, 9A, and 9B.

Referring still to FIGS. 15 and 16, in this exemplary embodiment, once the alternate arm 520 has been adjusted to a desired length by positioning the pinion 40 along the rack 42, movement of the pinion 40 is prevented (or "locked") by threading a locking pin 530 into the tongue 24*a* of the brace 20*b*. In this regard, the base 20*a* and the tongue 24*a* collectively define a channel 532 (illustrated in dashed lines in FIG. 15) in which the locking pin 530 can be threaded to prevent travel of the pinion 40 along the rack 42.

One of ordinary skill in the art will recognize that additional embodiments and implementations are also possible without departing from the teachings of the present invention. This detailed description, and particularly the specific details of the exemplary embodiments and implementations disclosed therein, is given primarily for clarity of understanding, and no unnecessary limitations are to be understood therefrom, for modifications will become obvious to those skilled in the art upon reading this disclosure and may be made without departing from the spirit or scope of the invention.

What is claimed is:

1. A lumbar process static and dynamic stabilization device for a spine, comprising:

an upper arm configured to receive and be affixed to a first spinous process of the spine;

a lower arm configured to receive and be affixed to a second spinous process of the spine, wherein the lower arm is pivotally connected to the upper arm, thereby allowing the device to be transitioned to a desired orientation; and a locking mechanism for securing the lower arm in the desired orientation relative to the upper arm;

wherein a fastener extends through an opening defined by the upper arm and a corresponding opening defined by the lower arm, forming a pivot connection between the upper arm and the lower arm;

wherein a second fastener extends through an elongated slot defined by the upper arm and an opening defined by the lower arm, such that the elongated slot defines a range in which the lower arm can move relative to the upper arm via the pivot connection;

wherein a length of at least one of the upper arm and the lower arm is adjustable, thus allowing for an increase in an overall length of the device;

wherein at least one of the upper arm and the lower arm includes a base and a brace, wherein the brace is configured to receive a spinous process of the spine, and wherein the brace is configured for movement with respect to the base, such movement allowing for adjustment of a length of the device, thereby allowing the device to span one or more vertebrae interspaces of the spine and to compress or distract across a space between the first spinous process to which the upper arm is secured and the second spinous process to which the lower arm is secured; and wherein at least one of the upper arm and the lower arm includes a rack and a pinion, with the pinion mounted for rotation with respect to and configured to effectuate movement of the brace with respect to the base.

2. The lumbar process static and dynamic stabilization device as recited in claim 1, wherein the second fastener can be tightened to provide a compressive force which resists pivoting of the lower arm with respect to the upper arm.

3. The lumbar process static and dynamic stabilization device as recited in claim 1, wherein the upper arm includes a first side portion and a second side portion which define a cavity configured to receive the first spinous process.

4. The lumbar process static and dynamic stabilization device as recited in claim 3, wherein either or both of the first side portion and the second side portion of the upper arm define one or more openings configured to receive screws to secure the upper arm to the first spinous process of the spine.

5. The lumbar process static and dynamic stabilization device as recited in claim 3, wherein either or both of the first side portion and the second side portion of the upper arm include bone spikes on interior surfaces thereof to assist in securing the upper arm to the first spinous process of the spine.

6. The lumbar process static and dynamic stabilization device as recited in claim 1, wherein the lower arm includes a first side portion and a second side portion which define a cavity configured to receive the second spinous process.

7. The lumbar process static and dynamic stabilization device as recited in claim 6, wherein either or both of the first side portion and the second side portion of the lower arm define one or more openings configured to receive screws to secure the lower arm to the second spinous process of the spine.

8. The lumbar process static and dynamic stabilization device as recited in claim 6, wherein either or both of the first side portion and the second side portion of the lower arm include bone spikes on interior surfaces thereof to assist in securing the lower arm to the second spinous process of the spine.

9. The lumbar process static and dynamic stabilization device as recited in claim 1, and further comprising a second locking mechanism, which can be selectively engaged to maintain the positioning of the pinion along the rack.

10. A lumbar process static and dynamic stabilization device for a spine, comprising:

an upper arm configured to receive and be affixed to a first spinous process of the spine;

a lower arm configured to receive and be affixed to a second spinous process of the spine, wherein the lower arm is pivotally connected to the upper arm, thereby allowing the device to be transitioned to a desired orientation;

wherein a length of at least one of the upper arm and the lower arm is adjustable;

wherein at least one of the upper arm and the lower arm includes a base and a brace, wherein the brace is configured to receive a spinous process of the spine, and wherein the brace is configured for movement with respect to the base, such movement allowing for adjustment of a length of the device, thereby allowing the device to span one or more vertebrae interspaces of the spine and to compress or distract across a space between the first spinous process to which the upper arm is secured and the second spinous process to which the lower arm is secured;

wherein at least one of the upper arm and the lower arm includes a rack and a pinion, with the pinion mounted for rotation with respect to and configured to effectuate movement of the brace with respect to the base;

a first locking mechanism for securing the lower arm in the desired orientation relative to the upper arm; and a second locking mechanism, which can be selectively engaged to maintain the positioning of the pinion along the rack, wherein the second locking mechanism is defined by a first base plate of the base, a second base plate of the base, and a fastener that can be engaged to draw the first base plate and the second base plate toward each other to clamp the pinion.

11. A lumbar process static and dynamic stabilization device for a spine, comprising:

an upper arm configured to receive and be affixed to a first spinous process of the spine;

a lower arm configured to receive and be affixed to a second spinous process of the spine, wherein the lower arm is pivotally connected to the upper arm, thereby allowing the device to be transitioned to a desired orientation;

wherein a length of at least one of the upper arm and the lower arm is adjustable;

wherein at least one of the upper arm and the lower arm includes a base and a brace, wherein the brace is configured to receive a spinous process of the spine, and wherein the brace is configured for movement with respect to the base, such movement allowing for adjustment of a length of the device, thereby allowing the device to span one or more vertebrae interspaces of the spine and to compress or distract across a space between the first spinous process to which the upper arm is secured and the second spinous process to which the lower arm is secured;

wherein at least one of the upper arm and the lower arm includes a rack and a pinion, with the pinion mounted for rotation with respect to and configured to effectuate movement of the brace with respect to the base;

a first locking mechanism for securing the lower arm in the desired orientation relative to the upper arm; and a second locking mechanism, which can be selectively engaged to maintain the positioning of the pinion along the rack, wherein the second locking mechanism is defined by a plate and one or more fasteners, whereby tightening of the one or more fasteners draws the plate against the pinion to restrict movement thereof.

12. A lumbar process static and dynamic stabilization device for a spine, comprising:

an upper arm configured to receive and be affixed to a first spinous process of the spine;

a lower arm configured to receive and be affixed to a second spinous process of the spine, wherein the lower arm is pivotally connected to the upper arm, thereby allowing the device to be transitioned to a desired orientation;

wherein a length of at least one of the upper arm and the lower arm is adjustable;

wherein at least one of the upper arm and the lower arm includes a base and a brace, wherein the brace is configured to receive a spinous process of the spine, and wherein the brace is configured for movement with respect to the base, such movement allowing for adjustment of a length of the device, thereby allowing the device to span one or more vertebrae interspaces of the spine and to compress or distract across a space between the first spinous process to which the upper arm is secured and the second spinous process to which the lower arm is secured;

wherein at least one of the upper arm and the lower arm includes a rack and a pinion, with the pinion mounted for rotation with respect to and configured to effectuate movement of the brace with respect to the base;

a first locking mechanism for securing the lower arm in the desired orientation relative to the upper arm; and a second locking mechanism, which can be selectively engaged to maintain the positioning of the pinion along the rack, wherein the brace includes a tongue to which the pinion is mounted, and the second locking mechanism is defined by one or more fasteners, whereby tightening of the one or more fasteners moves the pinion out of alignment with the rack, thus preventing movement of the pinion relative to the rack.

13. A lumbar process static and dynamic stabilization device for a spine, comprising:

an upper arm configured to receive and be affixed to a first spinous process of the spine;

a lower arm configured to receive and be affixed to a second spinous process of the spine, wherein the lower arm is pivotally connected to the upper arm, thereby allowing the device to be transitioned to a desired orientation;

wherein a length of at least one of the upper arm and the lower arm is adjustable;

wherein at least one of the upper arm and the lower arm includes a base and a brace, wherein the brace is configured to receive a spinous process of the spine, and wherein the brace is configured for movement with respect to the base, such movement allowing for adjustment of a length of the device, thereby allowing the device to span one or more vertebrae interspaces of the spine and to compress or distract across a space between the first spinous process to which the upper arm is secured and the second spinous process to which the lower arm is secured;

wherein at least one of the upper arm and the lower arm includes a rack and a pinion, with the pinion mounted for rotation with respect to and configured to effectuate movement of the brace with respect to the base;

a first locking mechanism for securing the lower arm in the desired orientation relative to the upper arm; and a second locking mechanism, which can be selectively engaged to maintain the positioning of the pinion along the rack, wherein the brace includes a tongue to which the pinion is mounted, and wherein the second locking mechanism includes a locking pin which can be selectively threaded into a cavity within the tongue to prevent travel of the pinion along the rack.

* * * * *